United States Patent
Chennubhotla et al.

(10) Patent No.: US 11,972,858 B2
(45) Date of Patent: Apr. 30, 2024

(54) SYSTEM AND METHOD FOR CHARACTERIZING CELLULAR PHENOTYPIC DIVERSITY FROM MULTI-PARAMETER CELLULAR, AND SUB-CELLULAR IMAGING DATA

(71) Applicant: University of Pittsburgh—Of the Commonwealth System of Higher Education, Pittsburgh, PA (US)

(72) Inventors: Srinivas C. Chennubhotla, Pittsburgh, PA (US); Filippo Pullara, Pittsburgh, PA (US); Samantha A. Furman, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 347 days.

(21) Appl. No.: 17/605,423

(22) PCT Filed: May 13, 2020

(86) PCT No.: PCT/US2020/032637
§ 371 (c)(1),
(2) Date: Oct. 21, 2021

(87) PCT Pub. No.: WO2020/232094
PCT Pub. Date: Nov. 19, 2020

(65) Prior Publication Data
US 2022/0215935 A1    Jul. 7, 2022

Related U.S. Application Data

(60) Provisional application No. 62/847,622, filed on May 14, 2019.

(51) Int. Cl.
*G16H 30/40* (2018.01)
*G06F 18/23* (2023.01)
(Continued)

(52) U.S. Cl.
CPC ............. *G16H 30/40* (2018.01); *G06F 18/23* (2023.01); *G16H 10/40* (2018.01); *G16H 30/20* (2018.01)

(58) Field of Classification Search
None
See application file for complete search history.

(56) References Cited

U.S. PATENT DOCUMENTS

| | | |
|---|---|---|
| 9,984,199 B2 | 5/2018 | Sood et al. |
| 2009/0292482 A1 | 11/2009 | Frumkin et al. |

(Continued)

FOREIGN PATENT DOCUMENTS

| | | |
|---|---|---|
| WO | 2016201186 A1 | 12/2016 |
| WO | 2018222979 A1 | 12/2018 |

OTHER PUBLICATIONS

Laksameethanasan et al. "cellXpress: a fast and user-friendly software platform for profiling cellular phenotypes." In: BMC Bioinformatics vol. 14, Article No. S4 (2013), Oct. 22, 2013, [online] [retrieved on Aug. 6, 2020 (Aug. 6, 2020)] Retrieved from the Internet< URL: https://www.ncbi.nlm.nih.gov/pmdarticles/PMC3853218/ >, entire document.

(Continued)

*Primary Examiner* — Leon Flores
(74) *Attorney, Agent, or Firm* — Philip E. Levy; Eckert Seamans Cherin & Mellot LLC

(57) ABSTRACT

A method of characterizing cellular phenotypes includes receiving multi-parameter cellular and sub-cellular imaging data for a number of tissue samples from a number of patients or a number of multicellular in vitro models, performing cellular segmentation on the multi-parameter cellular and sub-cellular imaging data to create segmented multi-parameter cellular and sub-cellular imaging data, and performing recursive decomposition on the segmented multi-parameter cellular and subcellular imaging data to (Continued)

identify a plurality of computational phenotypes. The recursive decomposition includes a plurality of levels of decomposition with each level of decomposition including soft/probabilistic clustering and spatial regularization, and each cell in the segmented multi-parameter cellular and subcellular imaging data is probabilistically assigned to one or more of the plurality of computational phenotypes.

27 Claims, 5 Drawing Sheets

(51) Int. Cl.
*G16H 10/40* (2018.01)
*G16H 30/20* (2018.01)

(56) References Cited

U.S. PATENT DOCUMENTS

| | | |
|---|---|---|
| 2012/0035859 A1 | 2/2012 | Thomas |
| 2015/0198584 A1 | 7/2015 | Rajwa et al. |
| 2016/0341731 A1 | 11/2016 | Sood et al. |
| 2021/0233659 A1* | 7/2021 | Chennubhotla ...... G06V 20/698 |

OTHER PUBLICATIONS

Dong, Aoyan, "Analyzing Heterogeneity in Neuroimaging With Probabilistic Multivariate Clustering Approaches" (2017). Publicly Accessible Penn Dissertations. 3041, [Shortened] [online] [retrieved on Aug. 6, 2020 (Aug. 6, 2020)] Retrieved from the Internet < URL: https://repository.upenn.edu/edissertations/3041 >, entire document.

Ghahramani, Zoubin, and Geoffrey E. Hinton. The EM algorithm for mixtures of factor analyzers. vol. 60. Technical Report CRG-TR-96-1, University of Toronto, 1996. (Zoubin, 21996).

Dempster, A.P.; Laird, N.M.; Rubin, D.B. (1977). "Maximum Likelihood from Incomplete Data via the EM Algorithm". Journal of the Royal Statistical Society, Series B. 39 (1): 1-38.

Me. Tipping and C. Bishop, "Mixtures of probabilistic principal component analysers", Neural Computation 11(2),pp. 443-482. MIT Press.

Hallac, David, Jure Leskovec, and Stephen Boyd. "Network lasso: Clustering and optimization in large graphs." Proceedings of the 21th ACM SIGKDD International Conference on Knowledge Discovery and Data Mining. ACM, 2015. (Hallac, 2015).

M. T. Uhlik et al., "Stromal-Based Signatures for the Classification of Gastric Cancer," Cancer Res., vol. 76, No. 9, pp. 2573-2586, May 2016.

P. Elbischger, S. Geerts, K. Sander, G. Ziervogel-Lukas, and P. Sinah, "Algorithmic framework for HEp-2 fluorescence pattern classification to aid autoimmune diseases diagnosis," in 2009 IEEE ISBI, 2009, pp. 562-565. (Not Attached).

Y. Mei, R. Hontecillas, X. Zhang, A. Carbo, and J. Bassaganya-Riera, "Neural network models for classifying immune cell subsets," in IEEE ICBB, 2013, pp. 5-11.

A. Santamaria-Pang, J. Rittscher, M. Gerdes, and D. Padfield, "Cell segmentation and classification by hierarchical supervised shape ranking," in IEEE ISBI, 2015, pp. 1296-1299.

A. Santamaria-Pang et al, "Robust cell quantification of immune cell subtypes in histological samples," in IEEE EMBS International Conference on Biomedical and Health Informatics, 2017, pp. 121-124. (Not Attached).

ML. Nagy et al, "Efficient Large Scale Cell Classification and Analysis for MultiOmyx Assays: A Deep Learning Approach", AACR 2018.

Mckinley Eliot T. et al: "Optimized multiplex immunofluorescence single-cell analysis reveals tuft cell heterogeneity", JCI Insight, vol. 2, No. 11, Jun. 2, 2017 (Jun. 2, 2017), XP093010699, DOI: 10.1172/jci.insight.93487 Retrieved from the Internet: URL:https://www.ncbi.nlm.nih.gov/pmc/articles/PMC5453701 /pdf/ jciinsight-2-93487.pdf.

* cited by examiner

SYSTEM AND METHOD FOR CHARACTERIZING CELLULAR PHENOTYPIC DIVERSITY FROM MULTI-PARAMETER CELLULAR, AND SUB-CELLULAR IMAGING DATA

CROSS-REFERENCE TO RELATED APPLICATIONS

This application is a U.S. National Stage Application under 35 U.S.C. § 371 of International Application No. PCT/2020/032637, filed on May 13, 2020, entitled "SYSTEM AND METHOD FOR CHARACTERIZING CELLULAR PHENOTYPIC DIVERSITY FROM MULTI-PARAMETER CELLULAR AND SUB-CELLULAR IMAGING DATA", which claims priority under 35 U.S.C. § 119(e) from U.S. Provisional Patent Application No. 62/847,622, filed on May 14, 2019, entitled "UNSUPERVISED HIERARCHICAL LEARNING OF CELLULAR PHENOTYPIC DIVERSITY FROM IN SITU MULTI-PARAMETER CELLULAR AND SUB-CELLULAR IMAGING DATA," the contents of which are incorporated herein by reference.

GOVERNMENT CONTRACT

This invention was made with government support under grant #CA204826 awarded by the National Institutes of Health (NIH). The government has certain rights in the invention.

BACKGROUND OF THE INVENTION

1. Field of the Invention

The present invention pertains to digital pathology, and, in particular, to an unsupervised hierarchical learning system and method for characterizing and classifying the various cell types and their activations (cellular phenotypes) from multi-parameter cellular and sub-cellular imaging data (e.g., multi to hyperplexed imaging data) obtained from various imaging modalities.

2. Description of the Related Art

Digital pathology refers to the acquisition, storage and display of histologically stained tissue samples and is initially gaining traction in niche applications such as second-opinion telepathology, immunostain interpretation, and intraoperative telepathology. Typically, in digital pathology, a large volume of patient data, consisting of multiple slides, is generated from biopsy samples and is evaluated by a pathologist by viewing the slides on a high-definition monitor. Because of the manual labor involved, the current workflow practices are time consuming, error-prone and subjective.

Tissues are heterocellular systems with multiple different cell types spatially communicating with each other. One challenge for digital pathology is how to accurately and efficiently characterize the various cell types and their activations from multi-parameter cellular and sub-cellular imaging data obtained from various multi to hyperplexed imaging modalities.

SUMMARY OF THE INVENTION

In one embodiment, a method of characterizing cellular phenotypes from multi-parameter cellular and sub-cellular imaging data for a number of tissue samples from a number of patients or a number of multicellular in vitro models is provided. The method includes receiving segmented multi-parameter cellular and sub-cellular imaging data, wherein the segmented multi-parameter cellular and sub-cellular imaging data is generated by performing cellular segmentation on the multi-parameter cellular and sub-cellular imaging data, and performing recursive decomposition on the segmented multi-parameter cellular and subcellular imaging data to identify a plurality of computational phenotypes. The recursive decomposition includes a plurality of levels of decomposition with each level of decomposition including soft/probabilistic clustering and spatial regularization, and each cell in the segmented multi-parameter cellular and subcellular imaging data is probabilistically assigned to/owned by one or more of the plurality of computational phenotypes. More specifically, and for example, such probabilistic assignment/ownership means that a cell may have X % probability of belonging to phenotype A and Y % probability of belonging to phenotype B, and so on. In one particular implementation, cell may be deterministically assigned to only one of plurality of computational phenotypes for ease of visualization and interpretation.

In another embodiment, a computerized system for characterizing cellular phenotypes from multi-parameter cellular and sub-cellular imaging data for a number of tissue samples from a number of patients or a number of multicellular in vitro models is provided. The system includes a processing apparatus that includes a cellular phenotype characterizing component configured for receiving segmented multi-parameter cellular and sub-cellular imaging data, wherein the segmented multi-parameter cellular and sub-cellular imaging data is generated by performing cellular segmentation on the multi-parameter cellular and sub-cellular imaging data, and performing recursive decomposition on the segmented multi-parameter cellular and subcellular imaging data to identify a plurality of computational phenotypes. The recursive decomposition includes a plurality of levels of decomposition, with each level of decomposition including soft/probabilistic clustering and spatial regularization. Each cell in the segmented multi-parameter cellular and subcellular imaging data is probabilistically assigned to/owned by one or more of the plurality of computational phenotypes.

DETAILED DESCRIPTION OF EXEMPLARY EMBODIMENTS

Figure 1:
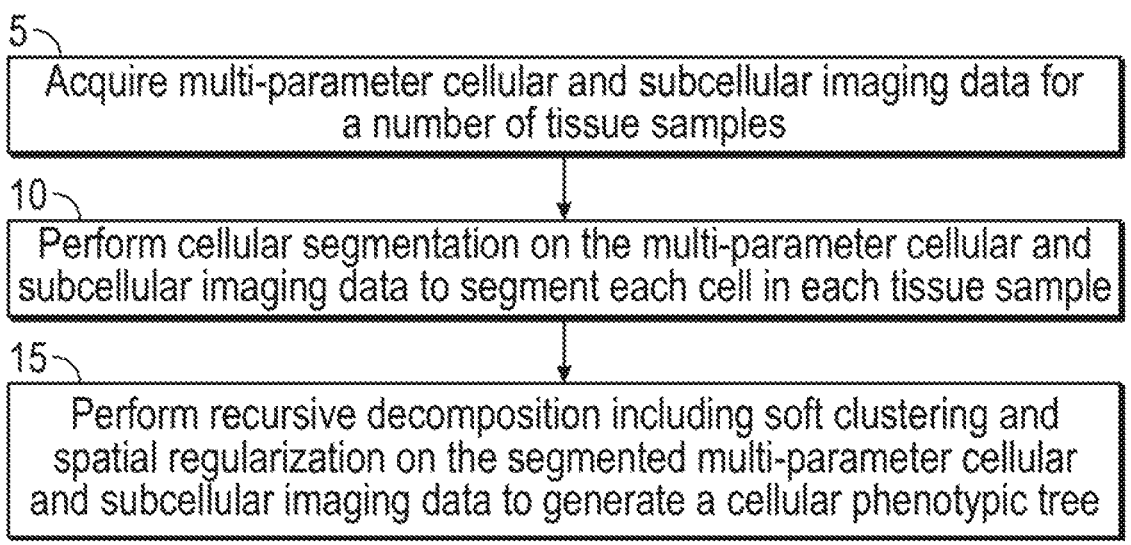
FIG. 1 is a flowchart of a method of characterizing cellular phenotypic diversity in multi to hyperplexed imaging data according to an exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed.

As used herein, the term "multiplexed imaging" shall refer to imaging techniques that employ up to 7 biomarkers, and "multiplexed images" shall to refer to images created using multiplexed imaging.

As used herein, the term "hyperplexed imaging" shall refer to imaging techniques that employ greater than 7 biomarkers, and "hyperplexed images" shall to refer to images created using hyperplexed imaging.

As used herein, the term "multi to hyperplexed imaging" shall include multiplexed imaging and/or hyperplexed imaging, and "multi to hyperplexed images" shall include multiplexed images and/or hyperplexed images.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject invention. It will be evident, however, that the disclosed concept can be practiced without these specific details without departing from the spirit and scope of this innovation.

The disclosed concept provides a novel unsupervised hierarchical learning technique to characterize cellular phenotypic diversity in multi to hyperplexed imaging data obtained from various imaging modalities. In the exemplary embodiment, the disclosed concept is described herein in connection characterizing and classifying the various cell types and their activations (cellular phenotypes) from multi-parameter cellular and sub-cellular imaging data in the form of hyperplexed immunofluorescence biomarker data. It will be understood, however, that this is meant to be exemplary only, and that the disclosed concept may be employed in connection with any spatial multi-parameter cellular and sub-cellular imaging data, including, without limitation, imaging data obtained using any of the following imaging modalities: transmitted light, combination of H&E and IHC (1 to multiple biomarkers); fluorescence; immunofluorescence (included but not limited to antibodies, nanobodies); live cell biomarkers multiplexing, hyperplexing; mass spectrometry (including but not limited to CyTOF); spatial transcriptomics (included but not limited to FISH); and electron microscopy. Targets include, without limitation, tissue samples (human and animal) and in vitro models of tissues and organs (human and animal).

As described in greater detail herein, one of the main ideas of the disclosed concept is that it employs data-driven phenotypes as opposed to user-defined phenotypes. More specifically, in the disease biology literature, it is very common for users to define a phenotype (user-defined phenotypes) along the following lines: biomarker A is positive, biomarker B is positive, biomarker C is negative; this implies phenotype X. This type of user definition of phenotypes means there is no data-driven phenotype that is discovered automatically. As discussed in detail herein, the disclosed concept permits data-driven phenotypes that are discovered automatically, and hence is very different from what is accepted in the field currently. Instead, the approach of the disclosed concept is unsupervised and is likely to identify user-defined phenotypes automatically. In addition, the approach of the disclosed concept is hypothesis generating in that it can identify and characterize novel phenotypes that have emerged in the data (data-driven phenotypes) because of disease progression.

Thus, as described in detail herein, the computational phenotyping methodology of the disclosed concept includes two steps, namely (i) soft/probabilistic clustering and (ii) spatial regularization, that are applied recursively (i.e., recursive decomposition) to the imaging data. In the exemplary embodiment, the results of the recursive decomposition are used to generate computational phenotypic trees wherein the terminal nodes of the tree (leaves) signify distinct computational phenotypes discovered in the input dataset. The distinct computational phenotypes form the components of the final multiple factor analysis (MFA) model determined by the recursive decomposition.

To account for the phenotypic diversity (e.g., epithelial enterocytes, myeloid macrophages, lymphoid T-cells, mesenchymal fibroblasts), the disclosed concept defines each cluster to be a hierarchical mixture of parametric low-dimensional subspaces. To account for phenotypic activation continuum (e.g., epithelial to mesenchymal transition), each cell is probabilistically owned by every one of the clusters in the tree. Further, the cluster assignments are spatially regularized to achieve spatial coherence that is respectful of tissue architecture. In addition, in the exemplary embodiment, the recursive decomposition is binary, i.e., the mixture model has two components at each level of the tree. The stopping criterion for recursion in the exemplary embodiment is a threshold applied on the angle between subspaces of the mixture model to ensure that the resulting phenotypes are distinct and to avoid overfitting. The disclosed concept, in the exemplary embodiment, also applies Kullback-Leiber (KL) divergence metrics using the MFA model parameters to further quantify the difference between any two computational phenotypes and visualize the spatial distribution of phenotypes within a tissue sample by assigning each cell to the phenotype with the highest ownership probability.

As noted above, the unsupervised machine learning algorithm of the disclosed concept recursively applies probabilistic clustering with a parametric mixture model, and spatial regularization of the resulting cluster assignments. In the exemplary embodiment, the probabilistic clustering algorithms include, but are not limited to, factor analyzers (FA), and probabilistic principal component analysis (PPCA). In addition, the probabilistic mixture models include, but are not limited to, mixtures of factor analyzers, Gaussian mixture models, and mixtures of PPCAs (MPPCA). In one particular implementation, the disclosed concept uses mixtures of factor analyzers, and learns the parameters of the model by an expectation-maximization algorithm.

Moreover, in another particular implementation, the disclosed concept employs a novel cost function for spatial regularization. Specifically, the objective cost function consists of two terms. The first term promotes sparsity in the cluster assignments, which implies each cell attempts to belong fully to one cluster. The second term promotes spatial coherence, which implies that if the cluster assignment of a cell is indefinite, then it seeks help from other cells in its neighborhood in updating its cluster assignment. Furthermore, there is an additional constraint in the objective function in that the cluster assignments for each cell should sum to 1. Also, for promoting spatial coherence, each cell is connected to its neighbors within a cut-off distance. The disclosed concept may also use the alternating directions method of multipliers (ADMM) approach.

Because of probabilistic assignment of cells to clusters, in the exemplary embodiment, all levels of the hierarchy use all of the cellular data in building and evaluating the corresponding mixture models, except that the cells are now weighted appropriately. These weights also influence the spatial regularization step. To find the most discriminative biomarkers for the computationally derived phenotypes, the disclosed concept may perform a ranking operation on the biomarkers based on the differences in the mean vectors and subspace directions of the components in the mixture of factor analyzers model. Finally, the hierarchical construction terminates when the angle between the component subspaces of the mixture model is below a cut-off value.

FIG. 1 is a flowchart of a method of characterizing cellular phenotypic diversity in multi to hyperplexed imaging data according to an exemplary embodiment of the disclosed concept. Referring to FIG. 1, the method begins at step 5, wherein multi-parameter cellular and subcellular imaging data (in the form of hyperplexed immunofluorescence biomarker data in the non-limiting exemplary embodiment) is generated from multiple tissue samples from a cohort, which in the non-limiting exemplary embodiment is cancer patient cohort. It will be understood, however, that this is meant to be illustrative only and that the data could come from any patient cohort (i.e., any disease). More specifically, in the non-limiting exemplary embodiment, a plurality of HxIF image stacks are generated from formalin-fixed paraffin-embedded (FFPE) tissue microarrays (TMAs) from resected tissue samples obtained from the patient cohort. As will be appreciated, generation of the HxIF image stacks involves, for each stack, the generation of a plurality of high resolution multiplexed images from each tissue section using a multiplexed (specifically hyperplexed in this embodiment) imaging process that includes repeated labeling of each tissue section with a number of fluorescent tags to image a plurality of biomarkers.

In the non-limiting exemplary embodiment described herein for illustrative purposes, the multi-parameter cellular and subcellular imaging data acquired in step 5 of FIG. 1 may be generated using the GE Healthcare Cell DIVE™ (previously named MultiOmyx) HxIF imaging and image processing workflow instrument. This is meant to be exemplary only, and it will be understood that the multi-parameter cellular and subcellular imaging data may be generated using other known or hereafter developed techniques.

The Cell DIVE™ system of the exemplary embodiment can perform hyperplexed imaging of greater than 50 biomarkers via sequentially multiplexed imaging of 2 to 3 biomarkers plus DAPI (4',6-diamidino-2-phenylindole) nuclear counterstain through iterative cycles of label-image-dye-inactivation. Extensive validation of this approach has demonstrated that a majority of epitopes tested are extremely robust to the dye inactivation process. It has been found that the biological integrity of the samples is preserved for at least 50 iterative cycles.

More specifically, in the exemplary embodiment, data generation using Cell DIVE™ involves non-destructive cyclical immunofluorescence labeling with two or three antibodies labeled with distinct fluorescent probes, imaging and subsequent quenching of the fluorescence. This process is repeated to capture all the required antibodies (biomarkers). In the exemplary embodiment, the data consists of image stacks taken at each region of interest and the overall image stack consists of several images for each of several imaging rounds. Each round includes a nuclear (DAPI) image that is used as a reference for registering all the images from all the rounds. Quantitation of images in each round includes the fluorescence intensity of each measured biomarker. Images are also acquired after quenching rounds for the purpose of autofluorescence removal. Processing of Cell DIVE images also includes correction for uneven illumination across the field of view, removal of autofluorescence, registration, and automated quality control (QC) detection of several categories of defects, including failed registration, blurred or saturated images, and other imaging issues. The images and data undergo a series of tissue and cell quality checks, log 2 transformation and normalization steps. To integrate data from batch processing, each biomarker is normalized to a control median. In the exemplary embodiment, images are acquired in TIFF format, while image metadata is captured in files having a simple structure that captures the provenance of which images were derived from which slides and characteristics of the acquisition. The biomarkers chosen are protein markers for specific cell lineages, oncogenes, tumor suppressors, and post-translational protein modifications indicative of cellular activation states. The data also includes corresponding clinical information including the histological tumor grade, cancer stage, gender, age, and follow up monitoring for 10 years.

In one particular non-limiting exemplary embodiment of the disclosed concept described herein for illustrative purposes, 56 particular biomarkers are used to generate the multi-parameter cellular and subcellular imaging data in step 5. It will be appreciated, however, that this is meant for illustrative purposes only and that more or less and/or different biomarkers may also be used within the scope of the disclosed concept.

Following step 5, the method proceeds to step 10. At step 10, cellular segmentation is performed on the acquired multi-parameter cellular and subcellular imaging data to segment each cell in each tissue sample. In the exemplary embodiment, cellular segmentation is done using a collection of structural biomarkers: NaKATPase (cell membrane, border), S6 (cytoplasm), and DAPI (nucleus). Protein expression and standard deviation are quantified by the median biomarker intensity value within each cell mask and transformed to the log 2 scale. Cells are filtered using individual QC scores generated for each cell (scores less than 0.7-0.8 will not be included, indicating inaccurate registration, misalignment or tissue loss) and based on number of pixels per segmented subcellular compartment.

Next, at step 15, recursive decomposition including soft/probabilistic clustering and spatial regularization at each level of decomposition is performed on the segmented multi-parameter cellular and subcellular imaging data. The recursive decomposition results in the creation of a cellular phenotypic tree in which each of the cells is probabilistically assigned to one or more of a plurality of computational phenotypes (i.e., each cell belongs to one or more computational phenotypes with a probability). In one particular implementation, each cluster/computational phenotype is defined to be a hierarchical mixture of parametric low-dimensional subspaces, and each cell is probabilistically owned by every cluster/computational phenotype.

Figure 2:
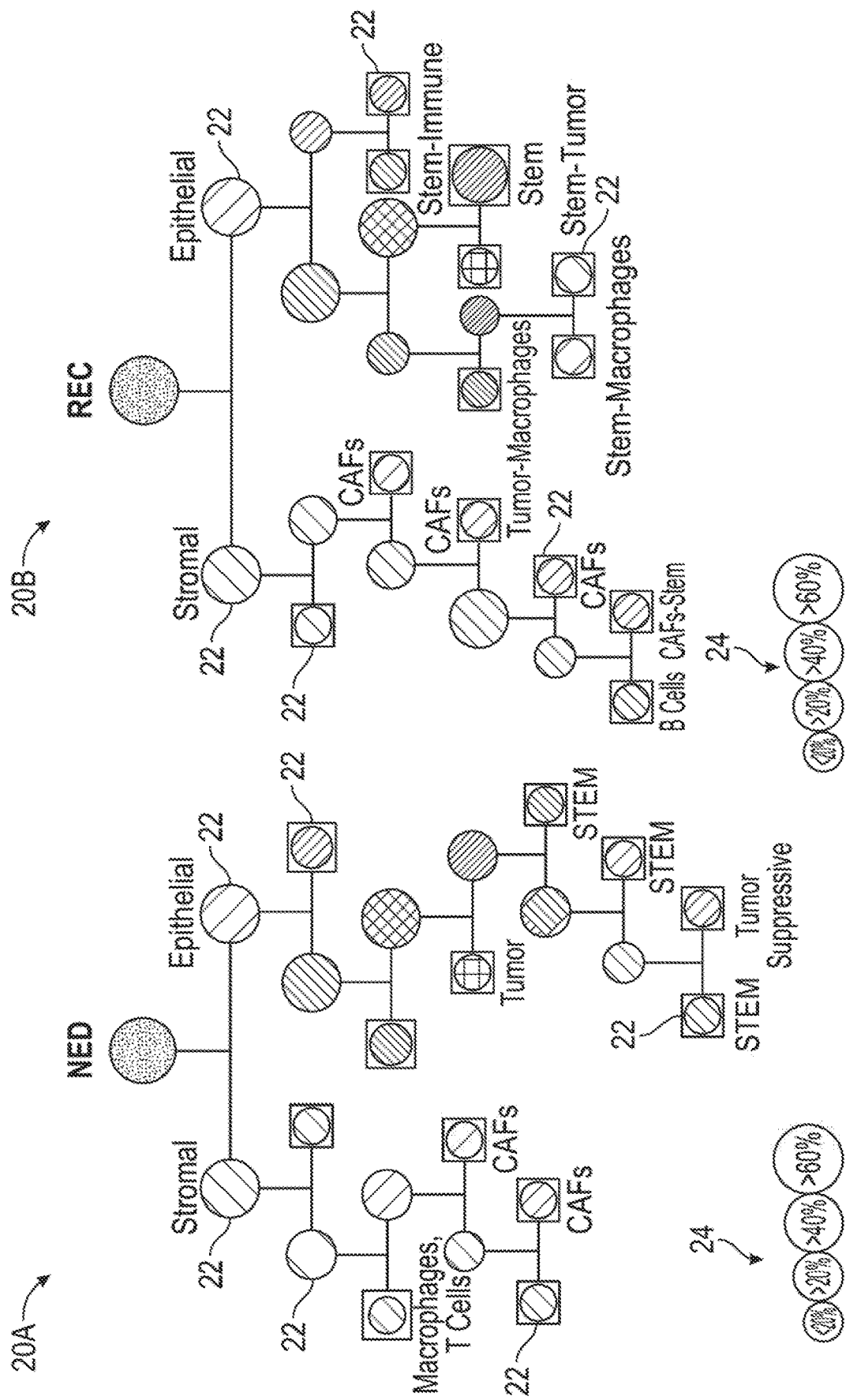
FIG. 2 is a schematic representation of exemplary cellular phenotypic trees for two exemplary sub-cohorts generated according the method of FIG. 1.

The methodology of the disclosed concept may be performed on an input of any size cohort. In one particular exemplary embodiment described herein for illustrative purposes, the disclosed concept was performed on sub-cohorts (NED, REC) of the original full cohort of cancer patients based on disease recurrence within 5 years. Exemplary cellular phenotypic trees 20A and 20B for the sub-cohorts generated according to step 15 of FIG. 1 are shown schematically in FIG. 2. In cellular phenotypic trees 20A and 20B, each node 22 (only certain example nodes are labeled 22 for ease of illustration) represents a computational phenotype and the size corresponds to the fraction of cells with majority ownership to that cluster/phenotype (based on size key 24 shown in FIG. 2). Terminal nodes 22 based on the stopping criteria are indicated with a black outline. Inferred biological labels are written when possible based on the set of discriminative biomarkers. Within each phenotype, cells are considered specialized (ownership probability >0.95) or non-specialized (ownership probability <0.95). The percentage of specialized and non-specialized cells within each phenotype is shown with respect to the entire data set (sum of all values equals 100%). Note, there exists a very small subset of non-specialized cells (7%) spread across all phenotypes. Although the size of each sub-cohort in this example is substantially different (NED=154, REC=59), the REC sub-cohort results in a larger heterogeneity of phenotypes supporting the well-known hyperproliferation property of tumors. In addition, these results demonstrate the hyperproliferation and differentiation which STEM cells undergo because the REC sub-cohort identifies three STEM-like phenotypes whereas the NED sub-cohort only identifies one.

Figure 3:
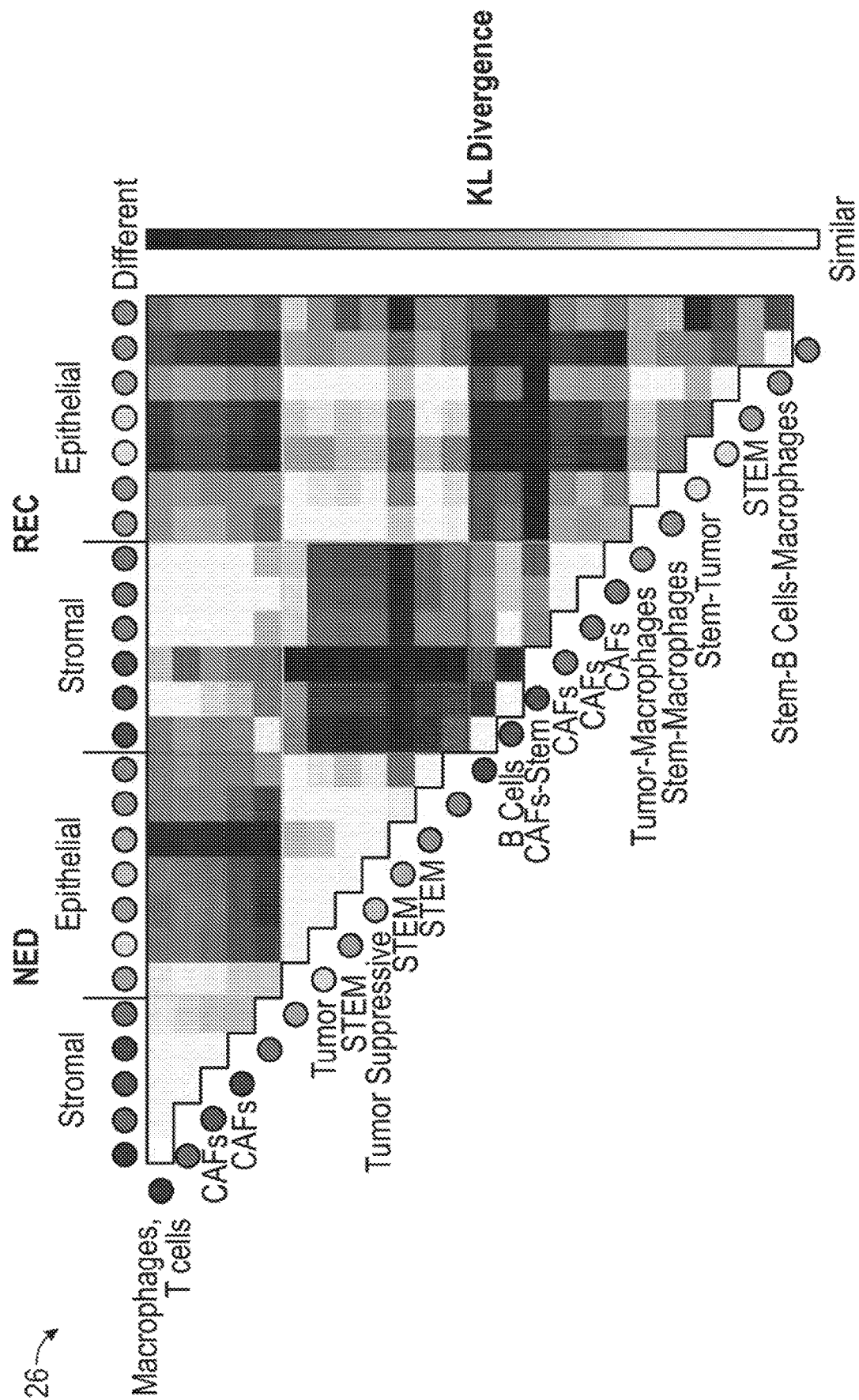
FIG. 3 is a schematic representation of an exemplary heat map that may be generated according to an aspect of the disclosed concept.
Figure 4:
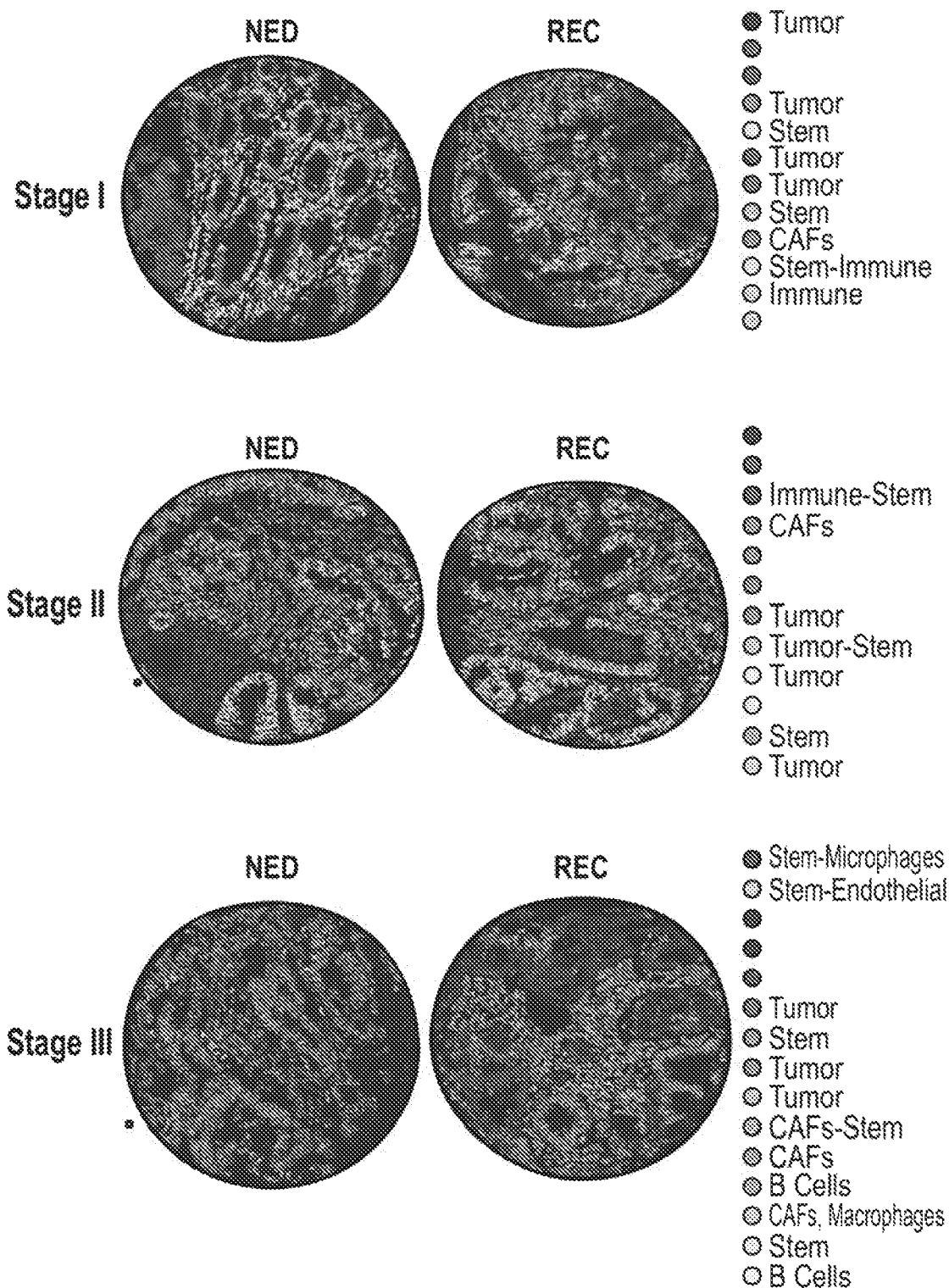
FIG. 4 is an exemplary image that may be generated according to an aspect of the disclosed concept wherein cell borders are color-coded based on sub-cohort results of the disclosed concept.

According to a further aspect of the disclosed concept, the difference between each pair of computational phenotypes is quantified using the Kullback-Leiber (KL) divergence metric. In particular, each computational phenotype can be considered a distribution described by a mean vector and a covariance matrix. KL divergence is a relative similarity ranking measure. The result is visualized in a heat map 26 shown schematically in FIG. 3 with separating lines indicating boundaries of each sub-cohort and the epithelial and stromal branches of each tree. The nodes along the horizontal and diagonal directions of this panel are the same and are color-coordinated to the corresponding tree. For convenience and discussion, the nodes along the diagonal include the manually inferred biological properties (where possible) based on the rank-ordered discriminant biomarkers. The similarities based on the KL divergence metric between epithelial-epithelial and stromal-stromal phenotypes demonstrates the stability and consistency of the method of the disclosed concept (e.g., biologically, epithelial computational phenotypes should be more similar than epithelial-stromal computational phenotypes). Also, this measure depicts the differences between phenotypes with similar inferred biological properties because the computational phenotypes are high-dimensional (e.g., STEM-STEM computational phenotypes are not identical based on KL divergence). Furthermore, tissue samples with cell borders color-coded based on the sub-cohort results of the disclosed concept for select representative Stage I, II, and III patients from each outcome-based cohort (NED, REC) may be visualized in image 28 shown in FIG. 4 (each cell can be assigned to one phenotype based on the highest ownership probability as discussed herein).

Moreover, in one particular exemplary embodiment described herein for illustrative purposes, step 15 is performed in the manner described below. It will be understood, however, that this is meant for illustrative purposes only and that alternative manners for performing step 15 are contemplated within the scope of the disclosed concept.

First, in this particular exemplary embodiment, the hyperplexed dataset is described in a high-dimensional space, where each cell $\vec{x}$ (p×1) is described by a p dimensional vector of biomarker expressions quantitated appropriately. Further, it is assumed that the hyperplexed dataset has an intrinsic low-dimensional representation. A mixture of factor analyzers described by low-dimensional factor loadings ($\Lambda$(p×k)), latent variables ($\vec{z}$ (k×1)), mean vector ($\mu$(p×1)), and noise term ($\vec{v}$ (p×1)): $\vec{x} = \partial \vec{z} + \vec{\mu} + \vec{v}$, where p is the number of biomarkers and k is the low-dimension latent space is used. The latent factors, $\vec{z}$, are generated from zero-mean, unit-variance Normal distribution N(0,I), and the noise term, $\vec{v}$ is sampled from N(0, $\Psi$). I is the unit variance and $\Psi$ is assumed to be a diagonal matrix. With this construction, $\vec{x}$ is distributed with zero mean and covariance $\Lambda\Lambda^T + \psi$ [8].

Soft Clustering

Typically, cellular phenotyping methods are constructed under the assumption that each cell belongs to one and only one cluster (hard clustering), leaving no room to identify specific cells that may belong to more than one phenotype due to an existing phenotypic continuum. With a Mixture of Factor Analyzers (MFA), the disclosed concept in this particular exemplary embodiment models the cells as M components (clusters) with the parameters ($\{\pi_j, \vec{\mu}_j, \Lambda_j\}_{j=1}^M$, $\Psi$) where $\pi_j$ is the component weight: $p(\vec{x}) = \Sigma_{j=1}^M N(\vec{x} | \vec{\mu}_j, \Lambda_j\Lambda_j^T + \Psi)$. A two-dimensional latent space is chosen for each component in the MFA model, as it has been observed this is enough to capture the input variance. The expectation-minimization (EM) algorithm is utilized to estimate the model parameters. The EM algorithm is initialized with a random set of parameters and the EM algorithm is not guaranteed to converge to a globally optimal solution. To account for this and ensure stability, the disclosed concept in this particular exemplary embodiment performs a hundred different EM optimizations, each initialized randomly. Each optimization yields an MFA model with a set of model parameters. The biomarker ranking for each set of model parameters (see discriminative biomarkers section) computed and all biomarker rankings are aggregated to compute their mean ranking. The model with a biomarker ranking closest (Euclidean distance) to the mean ranking is selected as the consensus model and deemed to provide an optimal subspace representation. The MFA model results in soft clustering probabilities—each cell, $x_c$, holds a unique probability of belonging to each cluster j, denoted as $\Omega_{cj}$.

Spatial Regularization

The soft clustering just described is agnostic to the spatial complexity of the TME, a key component driving intra-tumor heterogeneity (ITH). Based on properties of spatial ITH and the spatial tissue architecture of a tumor, neighborhoods of cells are expected to be spatially coherent (e.g., epithelial/tumor cells to be surrounded by, or spatially proximal to, other epithelial/tumor cells, but making allowance for the presence of tumor-infiltrating lymphocytes and other stromal cells for example). To promote specialization in cells, a spatial regularization component is added to optimize the ownership probabilities of non-specialized cells. The spatial regularization step optimizes the objective function which consists of two terms: ownership confidence and spatial coherence given by:

$$\min_{\Omega}\left(-\sum_{i=1}^{N}\sum_{j=1}^{M}\Omega_{cj}\log_2(\Omega_{cj}) + \lambda\sum_{(j,k)}w_{jk}\|\Omega_j - \Omega_k\|_2\right).$$

The first term minimizes the entropy of the ownership probabilities promoting specialization in cells. The second term promotes spatial coherence where $w_{jk}$ is the weight between cell i and cell j and is computed as the reciprocal of the distance between two cells:

$$w_{jk} = \frac{1}{dist(\text{cell}_i, \text{cell}_j)}.$$

A distance threshold (100 pixels at 0.5 µm/pixel) is used to eliminate an influence between cells that are too far apart to communicate.

The objective function is optimized using Alternating Directions Method of Multipliers (ADMM). It is assumed that the probability ownership confidence (term 1) and spatial coherence (term 2) should hold equal weight and therefore compute the tuning parameter, $\lambda$, to scale term 2 to the range of term 1:

$$\lambda = \frac{N_{opt} \times maxEntropy}{\sum_{(j,k)} w_{jk}}$$

where $N_{opt}$ is the number of cells being optimized and maxEntropy is the maximum value of the entropy function (=1). Relaxing the assumption that spatial coherence and ownership confidence should hold equal weight in the objective function would lead to a larger parameter space. A higher weight for spatial coherence results in homogenous neighborhoods and a larger set of non-specialized cells. On the contrary, a larger weight for ownership confidence results in the abolishment of all non-specialized cells. Stable and consistent results have been when the tuning parameter represents an equal weighting. Cells can only have neighbors within the same tissue sample and therefore, to increase computational speed and efficiency, spatial regularization is performed on each tissue sample independently.

Recursive Decomposition

To automate the process of phenotypic discovery in the disclosed concept in this particular exemplary embodiment, a recursive probabilistic approach is used where each step dissects the most dominant clusters with M=2 components. At each recursive step, the soft clustering step utilizes a low-dimensional latent space MFA. Subsequently, spatial regularization optimizes the resulting per-cell ownership probabilities to filter false-positive non-specialized cells by promoting ownership confidence and spatial coherence. The resulting parameters (ownership probabilities, $\Omega_j$, mean vector, $\vec{\mu}_j$, factor loadings, $\Lambda_j$) for each cluster, j, are passed to the next recursive step to decompose each cluster into further sub-clusters. This process is continued until an attempted cluster split invalidates any one of the following stopping criteria: 1) a resulting cluster takes ownership of <1% of cells, 2) the tree has surpassed a given depth threshold, or 3) the angle between the mean vectors and factor loading space are both below a given threshold.

Discriminative Biomarkers

Each recursive clustering or split in this particular exemplary embodiment results in two clusters with high dimensional mean vectors ($\vec{\mu}_1, \vec{\mu}_2$). To determine the discriminative ordering of the biomarkers, the method computes and sorts the proportional difference for each biomarker j: $\Delta_j = |\vec{\mu}_{1j} - \vec{\mu}_{2j}| * \max(\vec{\mu}_{1j}, \vec{\mu}_{2j})$. The absolute difference of the mean vectors may bias the selection of biomarkers with high biomarker value ranges and therefore, the method opts for a proportional difference to place the biomarkers on an even level for comparison.

Computational Phenotype Comparison

As noted elsewhere herein, the terminal nodes of the trees (i.e., leaves) signify distinct computational phenotypes discovered in the input dataset and form the components of the final MFA model determined by the recursive decomposition. From the MFA model, each computational phenotype, j, holds an ownership probability for each cell, c ($\Omega_{cj}$). With these ownership probabilities, the method in this exemplary embodiment computes the weighted mean ($\vec{\mu}_j$ (p×1)) and weighted covariance ($\Sigma_j$ (p×p)) to describe the computational phenotype. In addition, as noted elsewhere herein, the Kullback-Leiber divergence metric is a relative similarity ranking measure to compare any two distributions. Thus, the difference between any two pair of computational phenotypes is, in this embodiment, classified using the KL divergence metric. The KL divergence of two aussian multivariate distributions $N_0 \sim N(\vec{\mu}_0, \vec{\Sigma}_0)$, $N_1 \sim N(\mu_1, \Sigma_1)$ is:

$$D_{KL}(N_0\|N_1) = \frac{1}{2}\left(tr(\Sigma_1^{-1}\Sigma_0) + (\vec{\mu}_1 - \vec{\mu}_0)^T \Sigma_1^{-1}(\vec{\mu}_1 - \vec{\mu}_0) - p + \ln\left(\frac{\det(\Sigma_1)}{\det(E_0)}\right)\right).$$

KL divergence is not symmetric and the average KL divergence measure is calculated: $D_{KL}(N_0, N_1) = \frac{1}{2}(D_{KL}(N_0\|N_1) + D_{KL}(N_1\|N_0))$.

Common-Cell Comparison

In addition, in this particular embodiment, each cell can be assigned to one phenotype based on the highest ownership probability (cell-label). The cell-labels from two sets of derived computational phenotypes can be compared when the input cohorts have common tissue samples (e.g., ALL-DATA and Stage I). A confusion matrix may be calculated to compare the resulting cellular phenotypic labels. Specifically, for a cellular phenotype i and cellular phenotype j, the confusion matrix probability is as follows:

$$\frac{\text{\# of cells in } i \text{ and } j}{\text{\# of cells in } i}.$$

Systematic Selection of Representative Patients for Visualization

As noted above, in this embodiment, cells can be assigned to a computational phenotype based on the highest ownership probability value (cell-label). For C phenotypes, the method computes the fraction of each phenotype found in each patient, i, forming a vector $\vec{f}_i(C \times 1)$. When computing this fraction, the method only considers the specialized cells (ownership probability >0.95) to avoid the transitional and rare cells biasing the results. For each outcome-stage-based group (e.g., NED-Stage I, NED-Stage II, NED-Stage III), the method also computes the average phenotype fraction vector, $\vec{F}_{avg}$, and chooses the patient closest to the mean (Euclidean distance).

Figure 5:
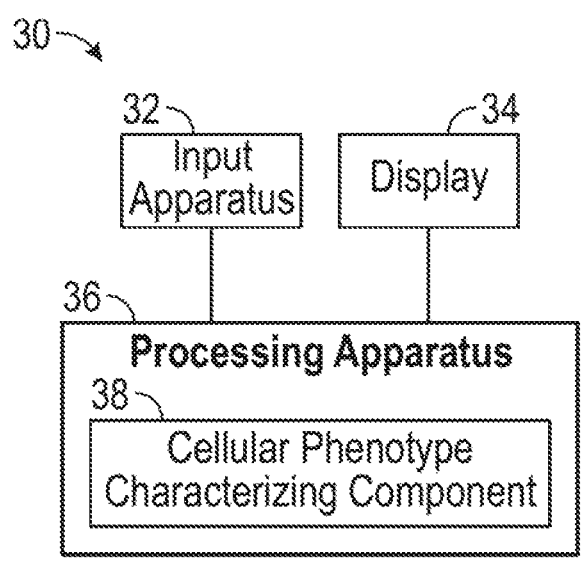
FIG. 5 is a schematic diagram of an exemplary digital pathology system for characterizing and classifying cell types and their activations (cellular phenotypes) from multi-parameter cellular and sub-cellular imaging data according to an exemplary embodiment of the disclosed concept.

FIG. 5 is a schematic diagram of an exemplary digital pathology system 30 for characterizing and classifying cell types and their activations (cellular phenotypes) from multi-parameter cellular and sub-cellular imaging data according to an exemplary embodiment of the disclosed concept as described herein. As seen in FIG. 5, system 30 is a computing device structured and configured to generate/receive the multi-parameter cellular and sub-cellular imaging data as described herein and process that data as described herein to characterize and classify cells. System 30 may be, for example and without limitation, a PC, a laptop computer, a tablet computer, or any other suitable device structured to perform the functionality described herein. System 30 includes an input apparatus 32 (such as a keyboard), a display 34 (such as an LCD), and a processing apparatus 36. A user is able to provide input into processing apparatus 36 using input apparatus 32, and processing apparatus 36 provides output signals to display 34 to enable display 34 to display information to the user as described in detail herein (e.g., the trees, heat maps and images described herein). Processing apparatus 36 comprises a processor and a memory. The processor may be, for example and without limitation, a microprocessor (pP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor, including routines for implementing the disclosed concept as described herein. In particular, processing apparatus 36 includes a cellular phenotype characterizing component 38 configured for classifying the various cell types and their activations (cellular phenotypes) from multi-parameter cellular and sub-cellular imaging data (e.g., multi to hyperplexed imaging data) obtained from various imaging modalities as described herein in the various embodiments.

Furthermore, the foregoing description of the disclosed concept is based on and utilizes in situ multi-parameter cellular and sub-cellular imaging data. It will be understood, however, that that is not meant to be limiting. Rather, it will be understood that the disclosed concept may also be used in conjunction with in-vitro microphysiological models for basic research and clinical translation. Multicellular in vitro models permit the study of spatio-temporal cellular heterogeneity and heterocellular communication that recapitulates human tissue that can be applied to investigate the mechanisms of disease progression in vitro, to test drugs and to characterize the structural organization and content of these models for potential use in transplantation.

Finally, while the disclosed concept has been described in connection with imaging data obtained from tumor sections, it will be understood that the disclosed concept may also be applied to imaging data that is obtained from other types of tissue sections and/or from un-sectioned tissue samples using imaging modalities that can penetrate into solid, un-sectioned samples.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of characterizing cellular phenotypes from multi-parameter cellular and sub-cellular imaging data for a number of tissue samples from a number of patients or a number of multicellular in vitro models, comprising:
   receiving segmented multi-parameter cellular and sub-cellular imaging data, wherein the segmented multi-parameter cellular and sub-cellular imaging data is generated by performing cellular segmentation on the multi-parameter cellular and sub-cellular imaging data; and
   performing recursive decomposition on the segmented multi-parameter cellular and subcellular imaging data to identify a plurality of computational phenotypes, wherein the recursive decomposition includes a plurality of levels of decomposition with each level of decomposition including soft/probabilistic clustering and spatial regularization, and wherein each cell in the segmented multi-parameter cellular and subcellular imaging data is probabilistically assigned to one or more of the plurality of computational phenotypes.

2. The method according to claim 1, further comprising generating a visual representation in which each cell in the segmented multi-parameter cellular and subcellular imaging data is probabilistically associated with only one of the plurality of computational phenotypes based on a respective highest ownership probability of each cell.

3. The method according to claim 1, further comprising generating a cellular phenotypic tree in which each cell in the segmented multi-parameter cellular and subcellular imaging data is probabilistically assigned to one or more of the plurality of computational phenotypes, wherein the cellular phenotypic tree includes a plurality of terminal nodes, with each of the terminal nodes signifying a respective one of the plurality of computational phenotypes.

4. The method according to claim 3, wherein a size of each terminal node corresponds to a fraction of the cells assigned to the computational phenotype of the terminal node.

5. The method according to claim 3, wherein the recursive decomposition employs a stopping criterion that stops recursion when: (i) a resulting cluster takes ownership of <1% of cells, (ii) it is determined that the cellular phenotypic tree has surpassed a given depth threshold, or (iii) an angle between mean vectors and factor loading space are both below a given threshold.

6. The method according to claim 1, wherein the multi-parameter cellular and sub-cellular imaging data comprises multi to hyperplexed immunofluorescence biomarker data or multi to hyperplexed mass spectrometry based biomarker data.

7. The method according to claim 1, further comprising using the plurality of computational phenotypes to form parameters of a multiple factor analysis (MFA) model.

8. The method according to claim 7, further comprising applying Kullback-Leiber (KL) divergence metrics using the parameters of the MFA model parameters to quantify a difference between any two of the computational phenotypes.

9. The method according to claim 8, further comprising generating a heat map based on results of the applying the KL divergence metrics.

10. The method according to claim 1, wherein the soft/probabilistic clustering includes a plurality of clusters, with each cluster corresponding to a respective one of the plurality of computational phenotypes, wherein each cluster is defined to be a hierarchical mixture of parametric low-dimensional subspaces, and wherein each cell in the segmented multi-parameter cellular and subcellular imaging data is probabilistically owned by every cluster.

11. The method according to claim 10, wherein the spatial regularization employs a function that includes a first term that promotes sparsity in cluster assignments and which implies that each cell attempts to belong fully to one of the clusters, and a second term that promotes spatial coherence.

12. The method according to claim 11, wherein the function is optimized using Alternating Directions Method of Multipliers (ADMM).

13. The method according to claim 1, wherein the recursive decomposition employs a stopping criterion for recursion comprising a threshold applied to an angle between the subspaces of the hierarchical mixture to ensure that the computational phenotypes are distinct.

14. A non-transitory computer readable medium storing one or more programs, including instructions, which when executed by a computer, causes the computer to perform the method of claim 1.

15. A computerized system for characterizing cellular phenotypes, comprising:
a processing apparatus, wherein the processing apparatus includes a cellular phenotype characterizing component configured for:
receiving segmented multi-parameter cellular and sub-cellular imaging data, wherein the segmented multi-parameter cellular and sub-cellular imaging data is generated by performing cellular segmentation on the multi-parameter cellular and sub-cellular imaging data; and
performing recursive decomposition on the segmented multi-parameter cellular and subcellular imaging data to identify a plurality of computational phenotypes, wherein the recursive decomposition includes a plurality of levels of decomposition with each level of decomposition including soft/probabilistic clustering and spatial regularization, and wherein each cell in the segmented multi-parameter cellular and subcellular imaging data is probabilistically assigned to one or more of the plurality of computational phenotypes.

16. The system according to claim 15, wherein the cellular phenotype characterizing component is further configured for generating a visual representation in which each cell in the segmented multi-parameter cellular and subcellular imaging data is probabilistically associated with only one of the plurality of computational phenotypes based on a respective highest ownership probability of each cell.

17. The system according to claim 15, wherein the cellular phenotype characterizing component is further configured for generating a cellular phenotypic tree in which each cell in the segmented multi-parameter cellular and subcellular imaging data is probabilistically assigned to one or more of the plurality of computational phenotypes, wherein the cellular phenotypic tree includes a plurality of terminal nodes, with each of the terminal nodes signifying a respective one of the plurality of computational phenotypes.

18. The system according to claim 17, wherein a size of each terminal node corresponds to a fraction of the cells assigned to the computational phenotype of the terminal node.

19. The system according to claim 17, wherein the recursive decomposition employs a stopping criterion that stops recursion when: (i) a resulting cluster takes ownership of <1% of cells, (ii) it is determined that the cellular phenotypic tree has surpassed a given depth threshold, or (iii) an angle between mean vectors and factor loading space are both below a given threshold.

20. The system according to claim 15, wherein the multi-parameter cellular and sub-cellular imaging data comprises multi to hyperplexed immunofluorescence biomarker data or multi to hyperplexed mass spectrometry based biomarker data.

21. The system according to claim 15, wherein the cellular phenotype characterizing component is further configured for using the plurality of computational phenotypes to form parameters of a multiple factor analysis (MFA) model.

22. The system according to claim 21, wherein the cellular phenotype characterizing component is further configured for applying Kullback-Leiber (KL) divergence metrics using the parameters of the MFA model parameters to quantify a difference between any two of the computational phenotypes.

23. The system according to claim 22, wherein the cellular phenotype characterizing component is further configured for generating a heat map based on results of the applying the KL divergence metrics.

24. The system according to claim 15, wherein the soft/probabilistic clustering includes a plurality of clusters, with each cluster corresponding to a respective one of the plurality of computational phenotypes, wherein each cluster is defined to be a hierarchical mixture of parametric low-dimensional subspaces, and wherein each cell in the segmented multi-parameter cellular and subcellular imaging data is probabilistically owned by every cluster.

25. The system according to claim 24, wherein the spatial regularization employs a function that includes a first term that promotes sparsity in cluster assignments and which implies that each cell attempts to belong fully to one of the clusters, and a second term that promotes spatial coherence.

26. The system according to claim 25, wherein the function is optimized using Alternating Directions Method of Multipliers (ADMM).

27. The system according to claim 15, wherein the recursive decomposition employs a stopping criterion for recursion comprising a threshold applied to an angle between the subspaces of the hierarchical mixture to ensure that the computational phenotypes are distinct.

* * * * *